Oct. 31, 1961 | E. W. MORING | Plant Pat. 2,099
PECAN TREE
Filed Jan. 8, 1960 | 2 Sheets-Sheet 1
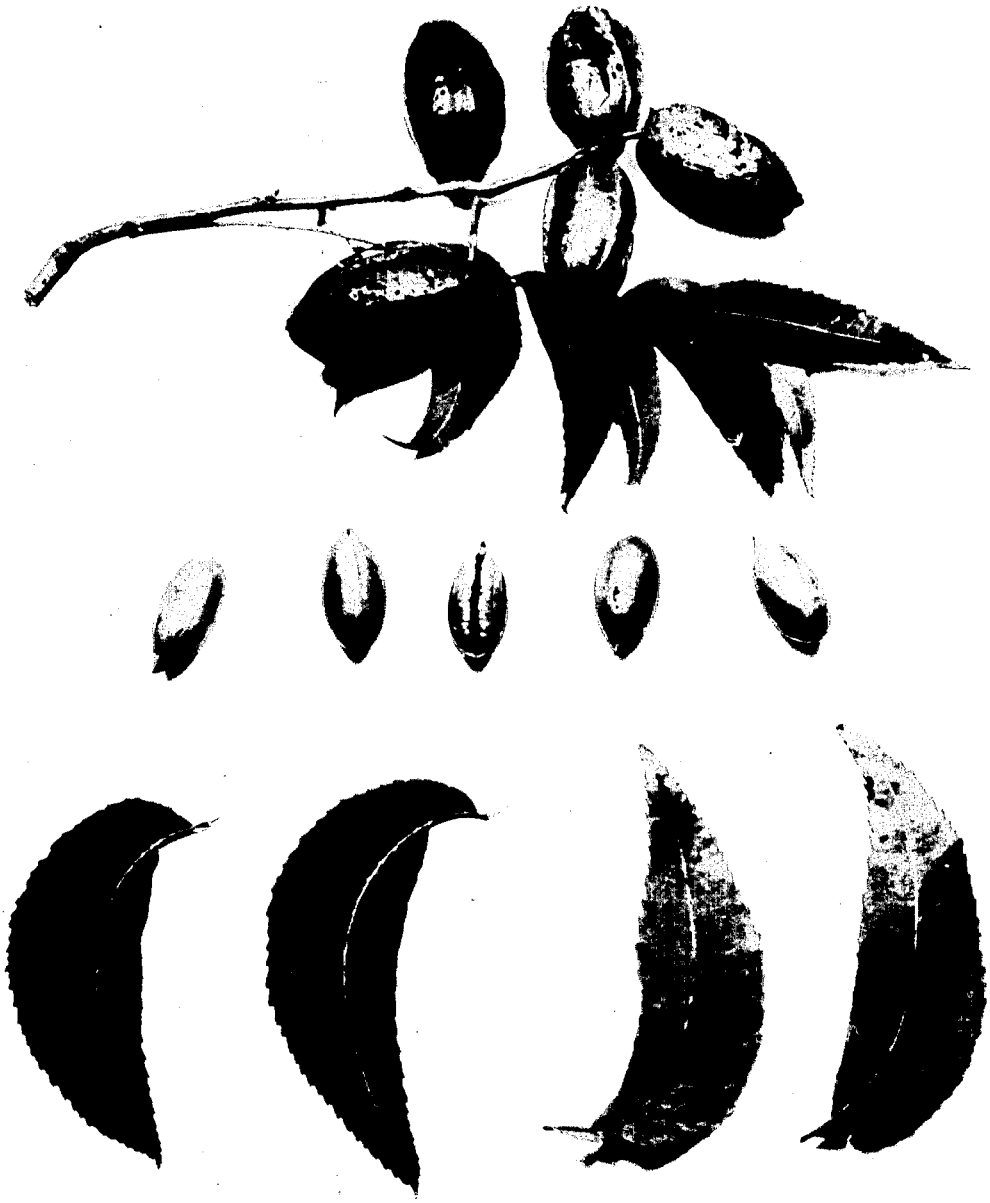
INVENTOR
E. W. Moring
BY Robb & Robb
ATTORNEYS PECAN TREE
Filed Jan. 8, 1960 2 Sheets-Sheet 2
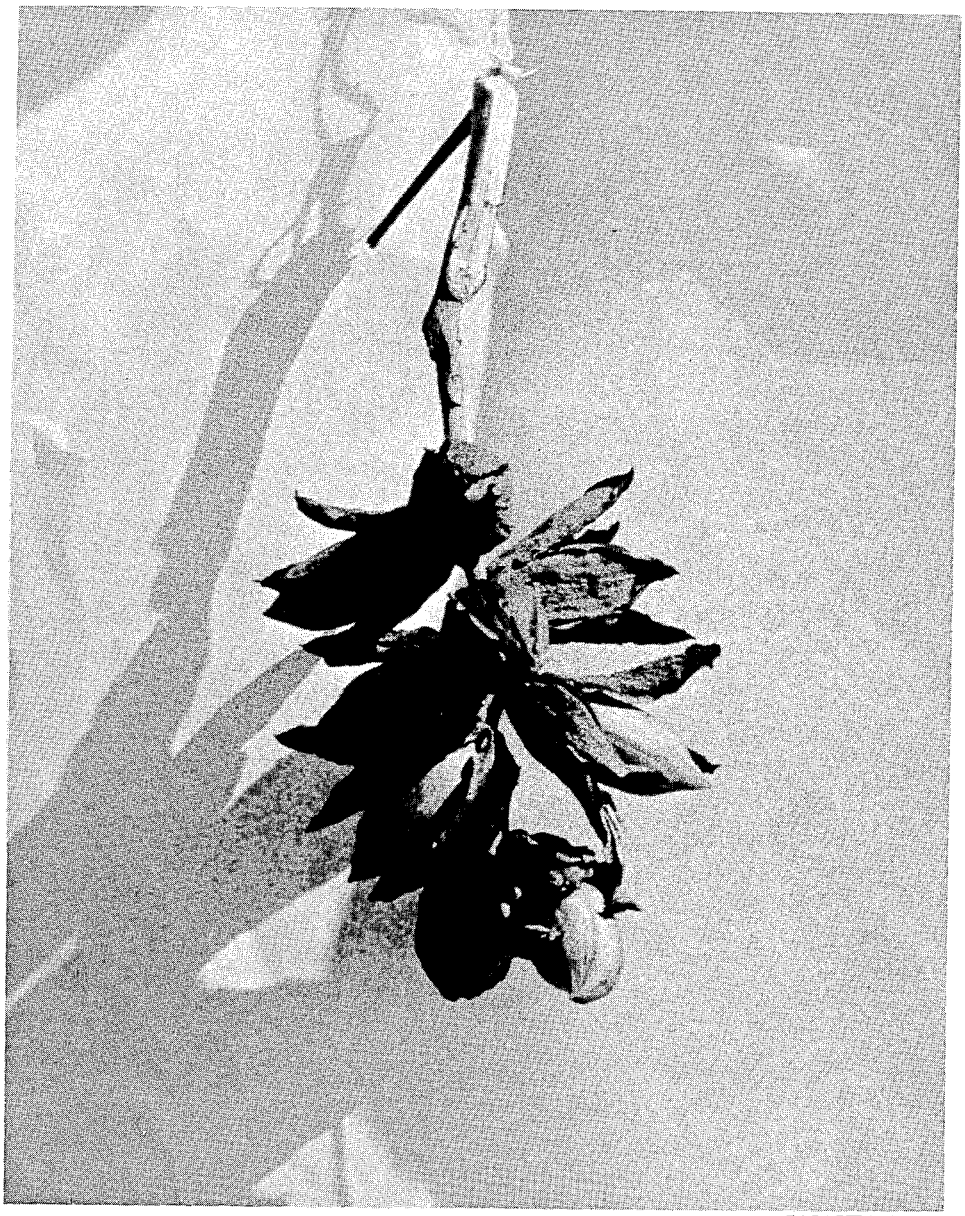
INVENTOR
Ernest W. Moring
BY Robb & Robb
ATTORNEYS United States Patent Office Plant Pat. 2,099
Patented Oct. 31, 1961

2,099
PECAN TREE

Ernest W. Moring, Pensacola, Fla., assignor to Simpson Nursery Company, Monticello, Fla., a partnership Filed Jan. 8, 1960, Ser. No. 1,394
1 Claim. (Cl. 47—62)

The present invention relates to a new and distinct variety of pecan tree, which was discovered by me as a newly found seedling on my farm property in Escambia County, near Pensacola, Florida.

The new seedling first appeared on open land near a pecan orchard on my farm referred to above and in which I was growing several standard pecan varieties. At first, no special significance was attributed to the new seedling, and it was set back for several years by regular cultivation with tractor discs of the land where the seedling was growing. Despite these adverse conditions, the seedling continued to grow, and my attention was ultimately focused thereon by my recognition that the tree had begun to bear nuts of superior quality, and by the additional unusual fact that the nuts were borne in clusters. I then realized that the seedling was different from any other variety formerly grown by me, as well as from any other variety of which I was aware, and I consequently took steps to carefully preserve the seedling and keep it under close observation.

In due course, asexual reproductions of the new seedling were made by me by budding the same on my own property near Pensacola, Florida, and still later, I arranged to have additional asexual reproductions made on my behalf by grafting, as performed by my assignee on the latter's nursery property at Monticello, Florida.

Continued observations of the original seedling and the various asexually reproduced progeny thereof fully confirmed the unusual and superior characteristics of the nuts which I had initially observed, as well as showed still other outstanding and distinctive characteristics, which altogether represent a unique and desirable combination which definitely differentiates my new pecan from all other varieties, and makes it a new and distinct variety of unknown parentage.

The dominant features of this unique combination referred to above may be briefly described, as follows:

(1) Abundant and attractive foliage, with consequent suitability for use as a shade tree;

(2) Consistently abundant nut production;

(3) A distinctive habit of bearing nuts in clusters;

(4) A distinctive grayish cast which is prominent in the color of both the nuts and the wood;

(5) A distinctive nut shape, characterized by a short point on the stem end and a long point on the opposite end;

(6) Easy and clean separability of the kernels from the nut shells and partitions;

(7) A plump form and attractive amber color of the kernels; and (8) Good resistance to pecan scab, as evidenced by the total absence of scab, and continued regular heavy bearing of nuts when other nearby standard varieties were failing and the nut crops of the latter were lost as the result of pecan scab.

The accompanying drawings show specimens of the foliage, wood and nuts, said nuts including both unshucked and shucked specimens, and one of the shucked nuts having its shell partially removed to expose the kernel, all as depicted in color, and an additional view of a natural nut cluster as depicted in black and white to illustrate the cluster bearing habit of the nuts.

The following is a detailed description of my new pecan variety, with color terminology in accordance with Koster's Color Guide, except where general color terms of ordinary dictionary significance are obvious, and as based upon observations made at both Pensacola and Monticello, Florida:

Tree: Medium size; good productivity; regular bearer; vigorous growth; medium-sized limbs. Wood—smooth; color—near Ashy Grey, Plate 99.

Foliage:

*Size.*—Large.

*Quantity.*—Abundant.

*Color.*—Upper side—near Holly Green, Plate 82. Under side—near Sage Green, Plate 78.

Buds:

*Shape.*—Long.

*Color.*—Grayish brown.

Nuts:

*Ripening habit.*—Even.

*Time of harvesting.*—Usually the month of October.

*Quantity.*—Abundant.

*Maturity.*—1st to 15th of October.

*Tenacity.*—Free.

*Cluster.*—Very large; from 3 to 11 nuts per cluster. Average number of nuts to cluster—4 or 5.

*Individual nuts.*—Shuck — color — near Boxwood Green, Plate 79. Size—medium; length—about 2 inches; diameter—about ⅞ inch. Average number of nuts to pound—about 32. Shape—long, with base from oblong to semi-pointed, and terminating in long point at opposite end. Shell—thin (about 1 mm.); cracks and releases very easily and cleanly; color—somewhat lighter than Van Dyck Brown, Plate 96, with grayish cast. Kernel: color—amber; flavor—excellent; shape — long; plump; texture—fine; sutures—even.

Disease resistance: Good resistance to pecan scab, as evidenced by comparison with other varieties grown under comparable cultural conditions in same locality at Pensacola, Florida.

Keeping Quality: Very good.

I claim:

A new and distinct variety of pecan tree, substantially as herein shown and described, characterized particularly as to novelty by the unique combination of abundant and attractive foliage and consequent suitability for use as a shade tree, consistently abundant nut production, a distinctive habit of bearing nuts in clusters, a prominent and distinctive grayish cast in the color of both the nuts and the wood, a distinctive nut shape evidenced by a short point on the stem end and a long point on the opposite end, easy and clean separability of the kernels from the nut shells and partitions, a plump form and attractive amber color of the kernels, and good resistance to pecan scab.

No references cited.